(12) United States Patent
Schaldach et al.

(10) Patent No.: US 6,899,914 B2
(45) Date of Patent: May 31, 2005

(54) METHOD OF APPLYING A MARKER ELEMENT TO AN IMPLANT AND AN IMPLANT PROVIDED WITH A MARKER ELEMENT (75) Inventors: Max Schaldach, deceased, late of Erlangen (DE); by Max Schaldach, Jr., legal representative, Berlin (DE); Klaus-Peter Schmitz, Rostock (DE); Jens Gobrecht, Gebenstorf (CH); Alexander Rzany, Nuernberg (DE); Detlef Behrend, Rostock (DE)

(73) Assignee: Biotronik Mess-und Therapiegeraete GmbH Ingeniurbuero Berlin (DE)

( * ) Notice: Subject to any disclaimer, the term of this patent is extended or adjusted under 35 U.S.C. 154(b) by 142 days.

(21) Appl. No.: 10/021,899

(22) Filed: Dec. 13, 2001

(65) Prior Publication Data

US 2002/0103528 A1 Aug. 1, 2002

(30) Foreign Application Priority Data

Dec. 18, 2000 (DE) .......................................... 100 64 596

(51) Int. Cl.⁷ ................................................ B05D 3/00
(52) U.S. Cl. ...................... 427/2.1; 427/2.24; 427/2.31; 427/157; 427/160; 427/180; 427/191; 427/230; 427/239; 427/372.2; 427/374.1; 427/375; 427/532; 427/551; 427/553; 427/554; 427/560; 427/600
(58) Field of Search ................................. 427/2.1, 2.24, 427/2.31, 532, 551, 553, 554, 560, 600, 157, 160, 180, 191, 230, 239, 372.2, 375, 374.1

(56) References Cited

U.S. PATENT DOCUMENTS

| 5,632,771 | A | | 5/1997 | Boatman |
| 5,741,327 | A | | 4/1998 | Frantzen |
| 6,022,374 | A | | 2/2000 | Imran |
| 6,162,244 | A | | 12/2000 | Braun |
| 6,287,332 | B1 | | 9/2001 | Bolz |
| 6,312,456 | B1 | | 11/2001 | Kranz |
| 6,379,381 | B1 | * | 4/2002 | Hossainy et al. .......... 623/1.42 |

FOREIGN PATENT DOCUMENTS

| DE | 35 22 737 A1 | 1/1987 |
| DE | 38 33 365 A1 | 4/1989 |
| DE | 197 07 642 A1 | 10/1997 |
| DE | 196 53 720 A1 | 6/1998 |
| DE | 197 31 021 A1 | 1/1999 |
| DE | 197 49 691 A1 | 4/1999 |
| DE | 198 56 983 A1 | 12/1999 |
| EP | 0 894 503 A2 | 2/1998 |
| WO | WO 97/33534 A1 | 9/1997 |
| WO | WO 99/15108 A2 | 4/1999 |

* cited by examiner

*Primary Examiner*—Elena Tsoy
(74) *Attorney, Agent, or Firm*—Hahn, Loeser + Parks, LLP; John J. Cunniff (57) ABSTRACT A method of applying a marker element (6; 6'; 6"; 25; 25'; 26; 28) to an implant (1; 1'; 1"; 1'''; 20; 20'), in particular a stent, intended for implantation in the human or animal body, comprising a main body and an opening (3; 3'; 3"; 3'''; 21; 21') provided in said main body (2; 2'; 2"; 2'''; 22; 22') for receiving the marker element (6; 6'; 6"; 25; 25'; 26; 28), wherein to form at least a part of the marker element (6; 6'; 6"; 25; 25'; 26; 28) a hardenable material or material mix is introduced into the opening and hardened therein.

7 Claims, 6 Drawing Sheets

METHOD OF APPLYING A MARKER ELEMENT TO AN IMPLANT AND AN IMPLANT PROVIDED WITH A MARKER ELEMENT

The present invention concerns a method of applying a marker element to an implant intended for implantation in the human or animal body, in particular a stent, comprising a main body and an opening provided in said main body for receiving the marker element. It further concerns an implant, in particular a stent, which is provided with such a marker element.

BACKGROUND OF THE ART

A large number of implants which are usual nowadays are inserted into the human or animal body for example with the assistance of a catheter or the like, without the surgeon being able to directly view the implantation location.

It is therefore frequently necessary for the correct position of the implant to be ascertained by other means. For that purpose, use is mostly made of imaging apparatuses which operate for example with X-rays and which enable the surgeon to judge the positioning of the implant, on the basis of the images obtained.

As many implant materials do not leave behind a sufficiently high-contrast image impression on the images obtained with the methods which are usual nowadays, in general so-called markers are applied to the implant at defined positions. The material of such markers is so selected that it affords a sufficiently high-contrast image impression, which permits conclusions to be drawn in regard to the position of the implant.

Markers of that kind generally comprise solid bodies which are impervious in regard to the radiation used for the imaging procedure. Such a solid body is inserted into the opening in the main body of the implant and connected to the main body by pressing or additionally or alternatively by welding.

Thus for example WO 97/33534 discloses a stent in which individual X-ray-opaque marker elements of gold are fitted into openings in the main body of the stent and are pressed to the latter in order to make a mechanical connection between the marker element and the main body of the stent. In that case the marker elements are in part also deformed in the manner of a rivet. Similar X-ray markers for a stent are known from U.S. Pat. No. 6,022,374. They are of an oversize in relation to the opening and are pressed into the opening, with deformation of the stent material delimiting the opening.

Both those alternative structures suffer from the disadvantage that the implant is subjected to in part really high mechanical loadings in the region of the opening, in the pressing operation. It is precisely in the case of the relatively fragile structures as are represented for example by stents that unwanted damage to the main body can rapidly occur in that region. That is particularly harmful because it cannot be immediately detected and possibly only causes failure to occur in the implanted condition. Thus for example in the case of a stent the structure may involve unwanted sharp broken edges which possibly even damage the surrounding tissue. It will be appreciated that equally the marker element may also come loose from the implant, which is undesirable.

In other known variants, the marker element is welded to the adjoining main body of the stent. That is known for example in relation to a stent from U.S. Pat. No. 5,632,771. Here, as moreover also in the case of the above-mentioned alternative configurations, there is the disadvantage that the opening and the marker element must be produced with a relatively accurate fit in order to ensure that a sufficient mechanical bond is achieved. All these variants therefore involve relatively expensive manufacture. In addition, in all known variants, the amount of freedom in terms of varying the geometry of the marker or the opening is restricted from economic points of view as different respective markers have to be produced for different openings.

SUMMARY OF THE INVENTION

The object of the present invention is therefore that of providing a method of the general kind set forth for applying a marker element to an implant as well as an implant of the general kind set forth, which do not suffer from the above-indicated disadvantages or which suffer therefrom at least to a lesser degree and which in particular ensure simple and flexible production.

That object is attained by a method of applying a marker element to an implant intended for implantation in a human or an animal body, where the implant comprises a main body and an opening provided in the main body for receiving the marker element. The method comprises the steps of introducing a hardenable material or material mix into the opening; and hardening the hardenable material or material mix therein to form at least a part of the marker element, wherein both the introducing step and the hardening step are effected by galvanic deposit. Alternately, the method comprises the steps of introducing a granular solid material or material mix into the opening, and sintering the granular solid material or material mix therein to form at least a part of the marker element.

The present invention is based on the technical teaching that particularly simple and flexible production of an implant with a marker element arranged in an opening in the main body of the implant is achieved if, to form at least a part of the marker element, a hardenable material or material mix is introduced into the opening and is hardened therein.

The material or material mix which is introduced into the opening is preferably a material or material mix which is capable of flow or which is capable of being poured. The flowability or pourability of the hardenable material or material mix used ensures on the one hand that the resulting marker element is readily adapted to any geometries of the opening. The consequence of this on the one hand is that there is a particularly high degree of flexibility in terms of the design configuration of the openings while on the other hand there is no need to observe particular dimensional tolerances or the like in the manufacture thereof. That considerably facilitates manufacture of the implant.

A further advantage of the concept in accordance with the invention is that, when applying the marker element, no excessively high stresses occur between the marker element and the adjoining main body of the implant, so that neither the marker element nor the main body of the implant are subjected to excessive mechanical loadings and in particular high prestressing effects. The probability that failure of the marker element or the adjoining main body occurs in manufacture or in use is thus considerably reduced in comparison with the structures known from the state of the art.

The material or material mix used may be any sufficiently biocompatible material or material mix, which is sufficiently hardenable to afford a sufficiently stable marker element and a sufficiently secure bond between the marker element and the adjoining main body.

In this respect the material or material mix used preferably forms the entire marker element. For that purpose it may comprise a single suitably hardenable component which in addition involves adequate opaqueness for the radiation used for the imaging procedure.

It is also possible for particles or relatively large pieces of a suitably radiation-opaque material to be added to a corresponding hardenable material or material mix. It is thus possible for example for the pourable material or material mix to comprise a granular material whose grains comprise one or more particles of a suitably radiation-opaque material, which are enclosed by a hardenable material or material mix. It is likewise possible for the opening to be filled with a suspension comprising a settable liquid material or material mix and such radiation-opaque particles. In the final result however it is also possible for relatively large pieces comprising such a radiation-opaque material to be entirely or partially enclosed by a corresponding hardenable material.

A further variant is represented by flowable or pasty, hardenable and suitably radiation-opaque materials such as for example the amalgam known from dentistry, which harden without the application of energy, that is to say cold. It will be appreciated that naturally these can also be used in conjunction with the specified enclosed or surrounded particles or pieces.

In all these variants it is only necessary to achieve a sufficiently strong and stable mechanical bond between the main body, the hardenable material or material mix and possibly the pieces comprising the radiation-opaque material. For that purpose, by means of a suitable configuration for the main body in the region which defines the opening or by virtue of using suitable molds and so forth when filling the opening with the flowable or pourable material or material mix, it is possible to produce undercut configurations between the main body and the resulting marker element, which undercut configurations afford a positively locking connection between the main body and the marker element. It is however equally possible for that strong and stable bond to be additionally or alternatively achieved by the flowable or pourable material or material mix being joined to the material of the main body during the hardening process. That can be effected by adhesion or by a material fusion effect, for example welding. Both plastic materials or plastic material mixes, metals or metal alloys and ceramics fall to be considered as materials for the hardenable material or material mix.

Preferred ones of the variants of the method according to the invention provide that the flowable or pourable material or material mix is a sinterable granular material or powder which is hardened in the opening by sintering as such a granular material or powder permits particularly easy handling.

Advantageous configurations of the method according to the invention are distinguished in that the hardening process includes an endothermic step and at least a part of the process energy in the endothermic step is introduced locally in the region of the opening. That makes it possible advantageously to achieve particularly specifically targeted and well-controllable hardening, with the result of affording both a strong and stable marker element and also a strong and stable join between the marker element and the main body.

In that respect, the process energy can be specifically targetedly locally introduced in any manner which is suited to the material or material mix to be hardened. Preferably the process energy is introduced in the endothermic step by targeted irradiation of the material or material mix which is arranged in the region of the opening. In that situation it is possible for example to use a laser as a laser can be employed in a particularly simple and well-targeted manner. It is however also possible to use any other alternative methods for introducing the process energy. Thus for example a powder or granular material can be excited to perform mechanical oscillations which then cause a rise in temperature by virtue of the friction between the particles. Such excitation can be effected for example by means of ultrasound. Equally however it is possible to use specifically suitably shaped heating surfaces or heating elements or the like. They can additionally be used to apply pressure to the material or material mix to be hardened. Such stamp or ram members etc for producing pressure can however naturally also be used in conjunction with the other alternative ways of introducing the energy.

In other variants at least a part of the process energy is introduced in the endothermic step electrically by producing a flow of current through the flowable or pourable material or material mix which is disposed in the region of the opening. In that case the material or material mix can be so selected that it represents a high resistance for the current, with the result that a large part of the supplied energy is converted therein into heat.

It will be appreciated that the listed options of introducing the process energy in the endothermic step can also be combined together in any desired fashion.

The present invention further concerns an implant, in particular a stent, for implantation in the human or animal body, comprising a marker element which is applied or produced in the above-described manner and which equally has the above-discussed advantages.

In particularly preferred variants of the implant according to the invention the opening and additionally or alternatively the marker element and additionally or alternatively the arrangement thereof, in relation to the main body, are adapted to identify at least one property of the implant. Equally however it is possible to provide such identification by virtue of the configuration or the arrangement of a marker element or a plurality of marker elements relative to each other. That may involve for example a product identification. It is likewise also possible to link any other items of information to an implant in that way. Thus for example the date of manufacture, the material and so forth of the implant can be identified in the manner indicated.

The invention also makes it possible at low cost to apply markings in the region of the implant, as are of particular interest. Thus for example in the case of a so-called bifurcation stent which is intended for use in the region of vessel branchings, it is possible for the lateral apertures to be easily identified in the manner indicated.

BRIEF DESCRIPTION OF THE DRAWINGS

Further preferred embodiments of the present invention are set forth in the appendant claims and are described hereinafter with reference to the accompanying drawings in which:

DETAILED DESCRIPTION OF THE INVENTION

Figure 1:
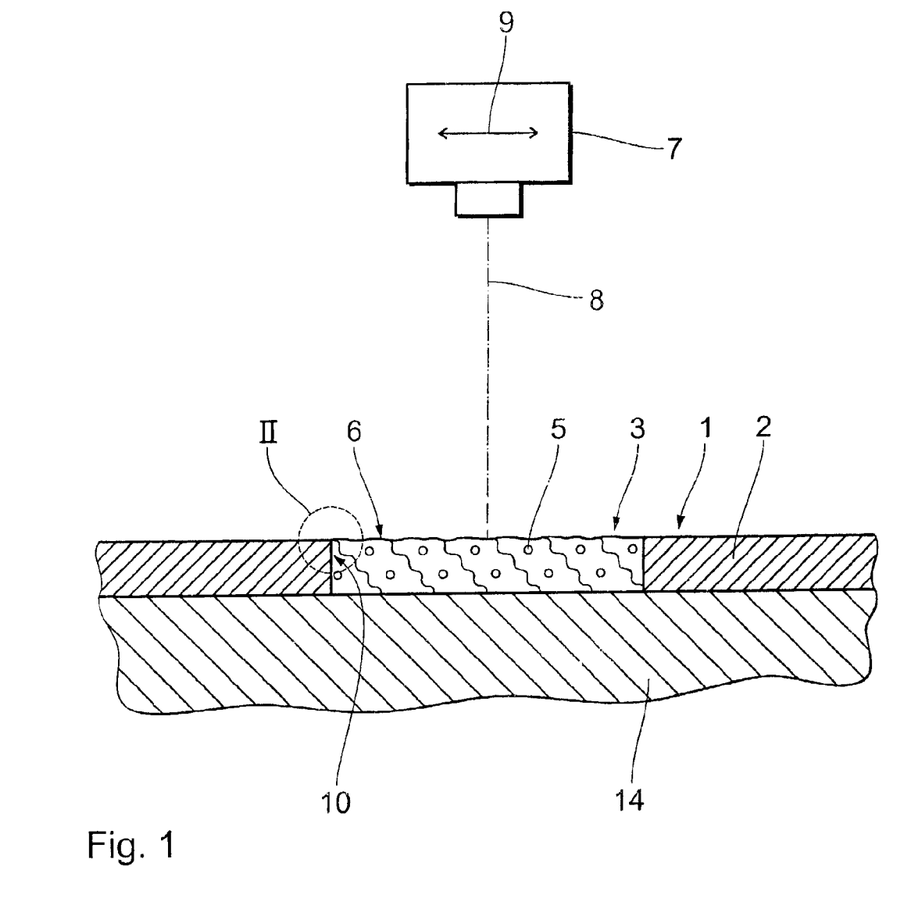
FIG. 1 is a diagrammatic partial view in section through an arrangement for carrying out a preferred variant of the method according to the invention.

FIG. 1 shows a diagrammatic partial view in section through an arrangement for carrying out a preferred variant of the method according to the invention, including an implant 1, in the main body 2 of which is provided an opening 3. A hardenable, pourable material mix in the form of a granular material 5 is introduced into the opening 3.

In the illustrated example the implant is a stent 1 having a tubular main body 2. It will be appreciated however that the invention can also be used in relation to any other implants. It will further be appreciated that in that respect it is possible to use any materials for the main body of the implant. It is only necessary for the flowable or pourable material or material mix to be suited thereto.

The hardened granular material 5 forms a marker element in the form of an X-ray marker 6. The granular material 5 is hardened in an operation which includes an endothermic step. In that endothermic step so much energy is applied to the granular material 5 that sintering of the grains of the granular material 5 takes place. In that case the grains of the granular material 5 melt at their surface and thus fuse together in the regions in which they bear against each other. In a further step the material cools down again and then, by virtue of the resulting joins between the grains of the granular material 5, forms a solid body which then forms the X-ray marker 6. That condition is shown in FIG. 2.

In order to harden the granular material 5 to constitute the X-ray marker 6, use is made of a laser 7 with which the granular material 5 is specifically targetedly irradiated in order to introduce the process energy for the endothermic step into the granular material 5. In that procedure the laser directs radiation on to the granular material 5 along its beam axis 8. The laser 7 can be displaced in the direction of the double-headed arrow 9 in order to feed sufficient process energy to the entire granular material 5. In that procedure the amount of radiation energy introduced in the edge region of the opening 3 is regulated in such a way that the material of the main body 2 is additionally caused to melt at the interface 10 between the granular material 5 and the main body 2. The grains 11 of the granular material 5 thus involve surface fusion to the main body 2 so that there is a kind of welded join between the X-ray marker 6 and the main body 2.

Figure 2:
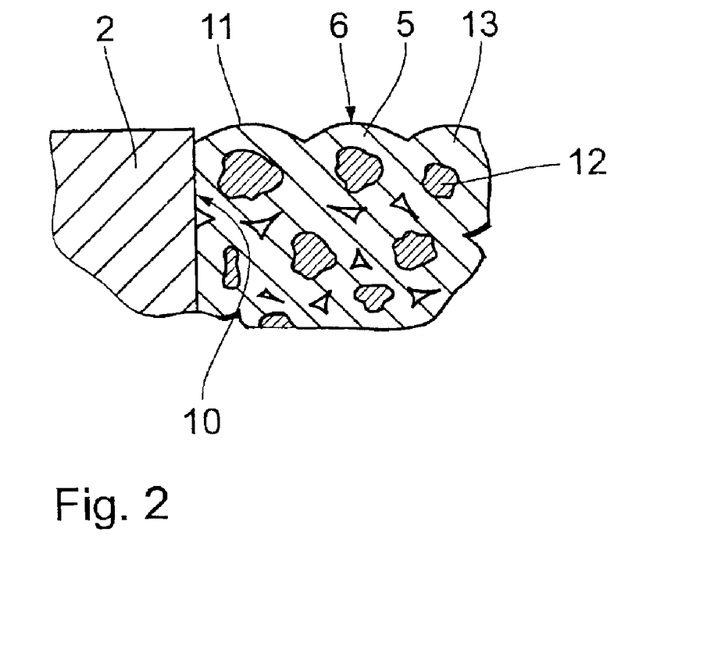
FIG. 2 shows a diagrammatic view in section of the detail indicated at II in FIG. 1.

As can be seen from FIG. 2, the granular material 5 comprises a material mix of X-ray-opaque particles 12 which are enclosed by a layer 13 of material which can be melted by the laser radiation. It will be appreciated however that, in other preferred variants, instead of a material mix, it is also possible to use powder grains or granular material grains, which can be melted at least at the surface, comprising a single material which is then suitably radiation-opaque.

The method of applying the X-ray marker 6 takes place in the following manner. In order to permit the granular material 5 to be introduced into the opening 3, the opening 3 which is open at both sides is closed at its underside by a closure element 14. Then, such a large amount of the granular material 5 is introduced into the opening 3 in the main body 2 of the implant 1 that the opening 3 is approximately completely filled. The procedure then involves the endothermic step in which energy is supplied by means of the laser in the above-described manner to the granular material 5 and to the edge region of the main body 2, which defines the opening 3. The sintered granular material then cools down again and thus forms the X-ray marker 6 which is fixedly joined to the main body 2.

Figure 3:
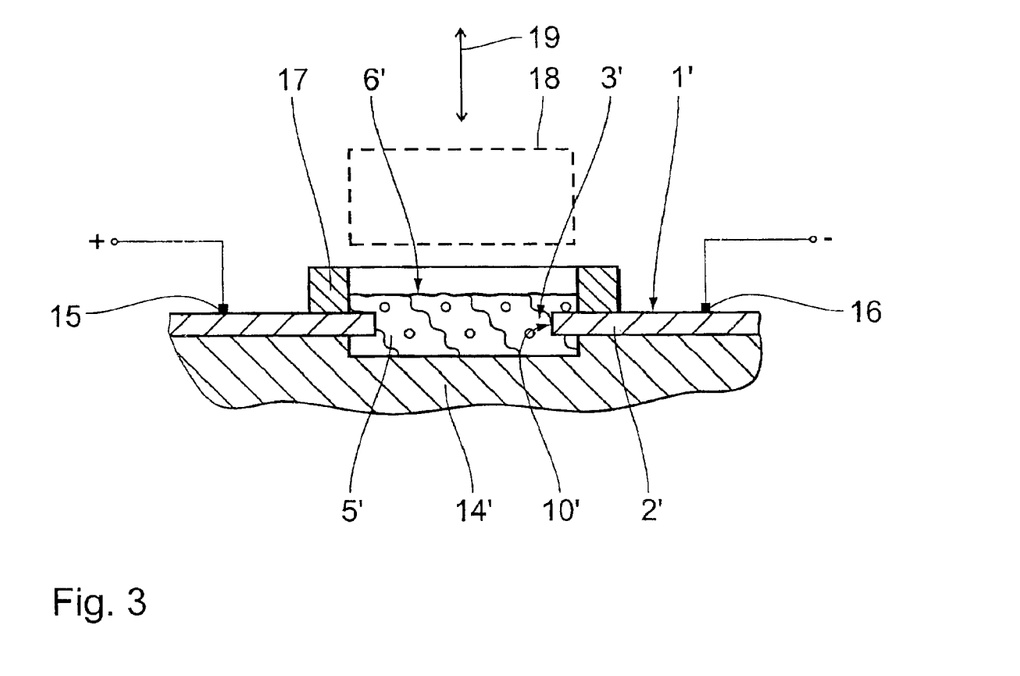
FIG. 3 is a diagrammatic partial view in section through an arrangement for carrying out a further preferred variant of the method according to the invention.

FIG. 3 shows an alternative arrangement for carrying out a variant of the method according to the invention. This is identical in terms of its fundamental operating procedure to that which was described with reference to FIGS. 1 and 2 so that here only the differences will be discussed.

One difference lies in the manner of introducing the process energy in the endothermic step of the method. In the illustrated example that energy is introduced by way of an electrical direct current by means of the contacts 15 and 16 which contact the electrically conductive main body 2' of the implant 1'. The contacts 15 and 16 are so arranged that the electrical direct current flows through the granular material 5'. The electrical resistance of the granular material 5' which in the illustrated example comprises grains of a single X-ray-opaque material is so high that a rise in temperature occurs as a consequence of the flow of current substantially in the entire granular material fill, and that rise in temperature ensures sintering of the grains of the granular material 5' in the manner described with reference to FIGS. 1 and 2.

An additional difference is that the edge regions 10' of the main body 2', which adjoin the opening 3', have a particularly high electrical resistance in order in that region to achieve a particularly high local heating effect which in turn results in local fusion of the grains of the granular material 5' to the main body 2', as described with reference to FIGS. 1 and 2. The high resistance was achieved in that respect by oxidation of those edge regions 10'. It will be appreciated however that it can also be implemented in any other manner.

A further difference in relation to the variant shown in FIG. 1 is that there is an additional shaping mold element 17. The mold element 17 is arranged in addition to the closure element 14' in the region of the upper aperture of the opening 3' in the main body 2' of the implant 1'. In this case the closure element 14' and the mold element 17 are of such a configuration and the filling amount of the granular material 5' is so selected that undercut configurations are afforded between the main body 2' and the X-ray marker 6'. In other words, this involves an X-ray marker 6' which embraces the edge region of the opening 3'.

In order to promote sintering of the granular material 5', it is possible to provide a punch or ram as is indicated by the broken-line contour 18 and which is displaceable along the arrow 19. Pressure can be applied to the granular material 5' in the sintering operation by means of the ram or punch in order to improve the sintering result.

It will be appreciated that, in other variants of the method in accordance with the invention, the closure element, the mold element and/or the punch or ram may also be individually or in combination in the form of heating elements in order to provide the process energy for the endothermic step.

It will further be appreciated that, in the illustrated example, the closure element 14' is of correspondingly smaller dimensions than the internal space of the stent so that, after manufacture of the X-ray marker 6', the closure element can be moved radially away from same and can be taken axially out of the stent.

Figure 4A:
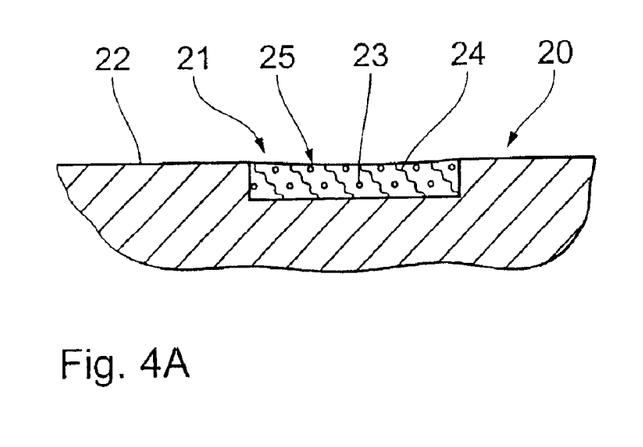
FIGS. 4A through 4D show diagrammatic partial views in section through preferred embodiments of the implant according to the invention.

FIG. 4A shows a variant of an implant 20 according to the invention with an opening 21 in the form of a recess in a main body 22. The opening 21 is filled with a flowable suspension of X-ray-opaque particles 23 in a settable plastic material 24, that suspension forming the X-ray marker 25 in the set condition.

Figure 4B:
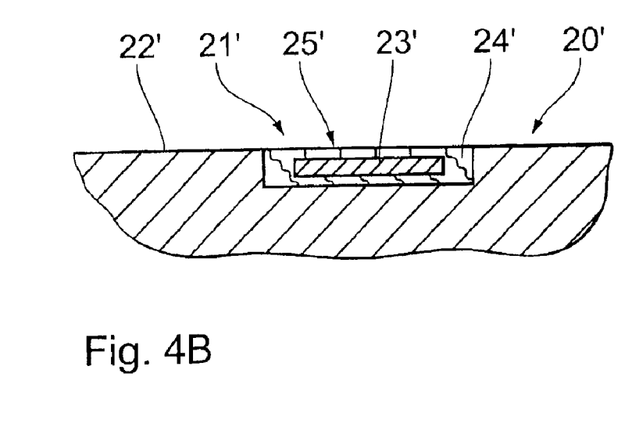

FIG. 4B shows a further variant of an implant 20' according to the invention with an opening 21' in the form of a recess in a main body 22'. The opening 21' is filled with a flowable settable plastic material 24' in which an X-ray-opaque element 23' is in turn embedded. The element 23' together with the set plastic material bed 24' forms the X-ray marker 25'.

Figure 4C:
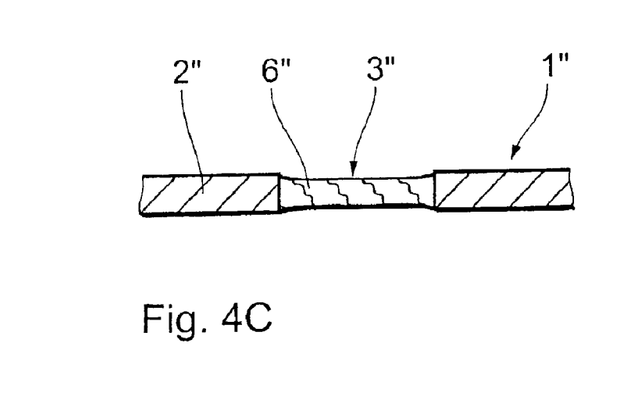

FIG. 4C shows a further variant of a stent 1" according to the invention. In this respect, the difference in relation to the stent shown in FIG. 1 is that the opening 3" in the main body 2" was filled in a dip process with a viscous suspension as was basically described in relation to FIG. 4A. In this case the join between the resulting X-ray marker 6" and the main body 2" is afforded by adhesion of the material of the X-ray marker 6" to the main body 2".

Figure 4D:
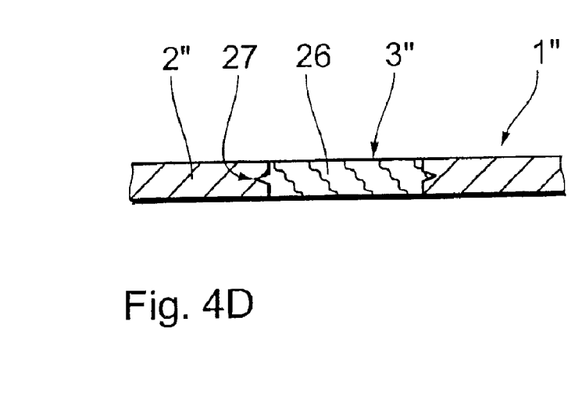

FIG. 4D shows a further variant of the stent 1" according to the invention with an X-ray marker 26. The difference in relation to the stent shown in FIG. 1 is on the one hand that the region of the main body 2" which defines the opening 3" has one or more undercut configurations 27 which ensure a positively locking join between the main body 2" and the X-ray marker 26.

A further difference is that the material used for the X-ray marker 26 is a cold-setting amalgam which is known from dentistry and which has excellent X-ray opacity. The material was introduced in its pasty, non-set condition into the opening 3''' and could then set there.

Figure 5:
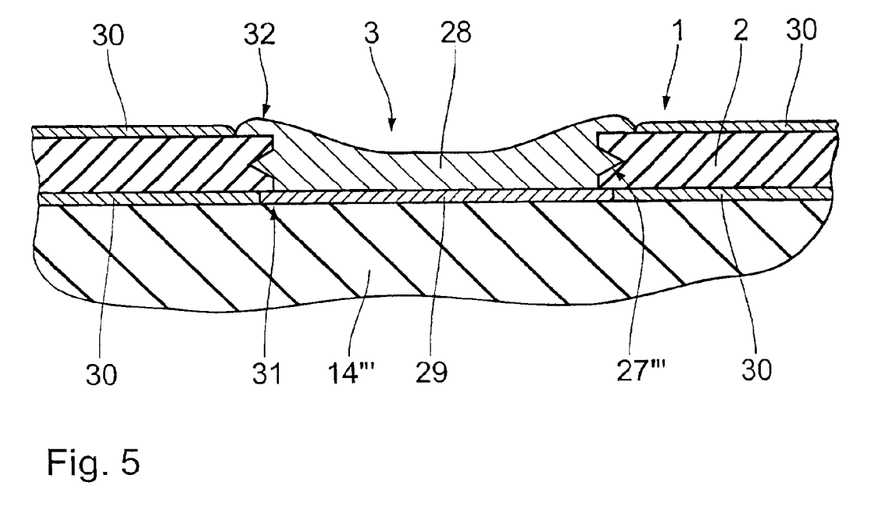
FIG. 5 shows a diagrammatic partial view in section through a further preferred embodiment of the implant according to the invention.

FIG. 5 shows a diagrammatic partial view in section through a further preferred embodiment of the implant according to the invention in the form of a stent 1''' having a main body 2''' in which there is an opening 3'''. An X-ray marker 28 was introduced into the opening 3''' by galvanic deposit of an X-ray-opaque material, in the present case gold, and hardened. The stent 1''' is shown in FIG. 5 in a condition in which the galvanic deposit has just been concluded.

To produce the X-ray marker 28 the stent 1''' is introduced into a galvanic solution in which a galvanic deposit process then takes place in known manner. In that case the main body 2''' of the stent 1''' forms a part of the deposit electrode at which the material of the X-ray marker 28 is deposited. In order to ensure that the opening 3''' is filled in the manner illustrated, a further part of the deposit electrode is formed by a thin conductive coating 29 on the closure element 14''' which is arranged in the interior of the stent 1''', which coating conductively contacts the edge region of the main body 2''' which delimits the opening 3'''.

It will be appreciated that, depending on the respective geometry of the opening, it is also possible to forego such a conductive coating or the like for filling the opening. On the contrary it is possible for the opening to 'grow over' even without such an ancillary means, in the course of the galvanic deposit procedure.

In order to prevent the material for the X-ray marker 28 being deposited on the entire main body 2''' of the stent 1''', the latter, in the regions in which no deposit is to take place, is provided with an easily removable protective coating 30 which prevents such a deposit from occurring. This may involve for example a wax or grease layer or the like.

Upon subsequent release of the closure element 14''' from the stent, the coating 29 remains adhering to the X-ray marker 28 and comes away from the closure element 14'''. That is particularly appropriate when the coating in any case comprises the same material as the X-ray marker 28 as that then ensures a particularly good join. On the other hand, the illustrated configuration affords an overlap 31 between the X-ray marker 28 and the main body 2''', which together with the overlap 32 between the X-ray marker 28 and the main body 2''' contributes to the strong mechanical join between the X-ray marker 28 and the main body 2'''.

A further mechanical fixing effect of that kind is afforded by the undercut configuration 27'''. It will be appreciated however that this does not necessarily have to be provided. Likewise it can replace the described overlap configurations. Furthermore the adhesive force of the X-ray marker material to the material of the main body may also be sufficiently great to ensure adequate fixing of the X-ray marker.

It will be appreciated moreover that the electrically conductive coating forming a part of the deposit electrode, in other variants of the invention, can also be released from the X-ray marker upon removal of the closure element so that then the X-ray marker only comprises the galvanically deposited material—possibly with the described inclusions therein and so forth.

It will further be appreciated that, as already described hereinbefore in particular with reference to FIG. 4B, the galvanically deposited material may also have embedded therein particles or pieces of another material or possibly even the same material.

Figure 6:
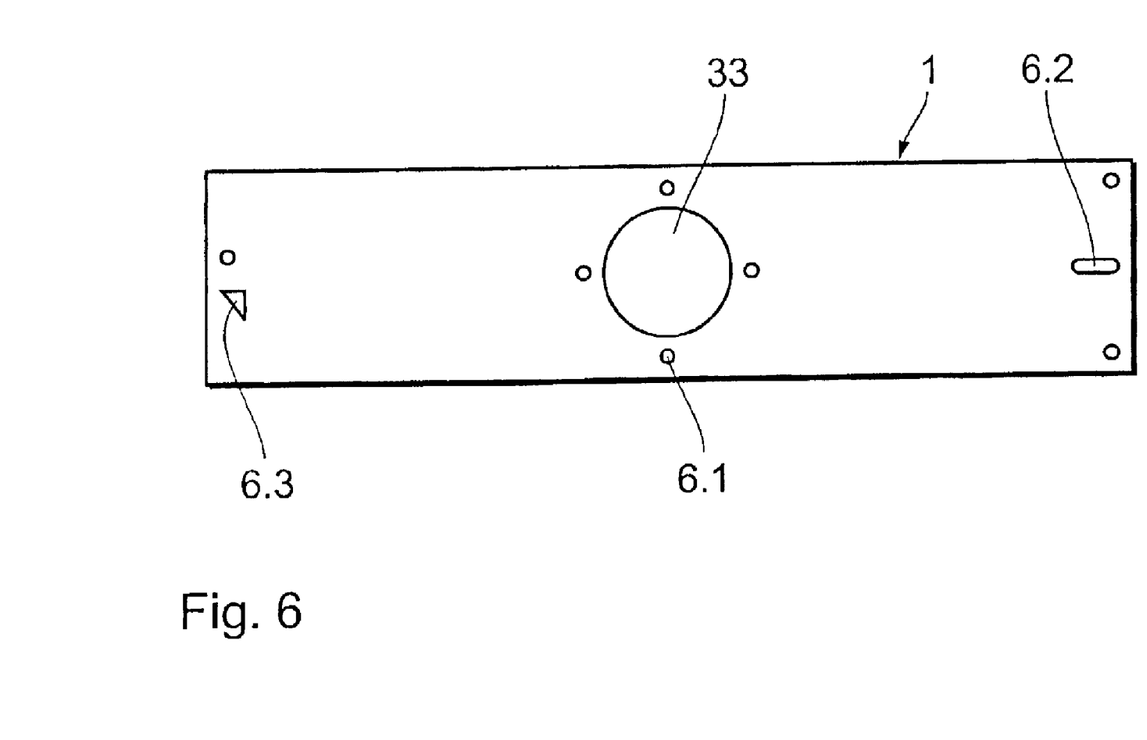
FIG. 6 is a diagrammatic plan view of a preferred embodiment of a stent according to the invention.

FIG. 6 shows a diagrammatic plan view of the stent 1 shown in FIGS. 1 and 2. This involves a so-called bifurcation stent which is used in the region of vessel branchings. For that purpose it has a lateral aperture 33 which is identified by X-ray markers 6.1.

At its two ends the stent 1 has further X-ray markers 6.2 and 6.3. They serve on the one hand to mark the ends of the stent 1. On the other hand, their configuration and the number of X-ray markers 6.2 and 6.3 respectively is so selected that they provide the surgeon with different items of information in relation to the stent. Thus the shape and number of the X-ray markers 6.2 provide information about the date of manufacture of the stent 1 while the shape and number of the X-ray markers 6.3 represent product identification for the stent. It will be appreciated that any other items of information relating to the stent can also be reproduced by the shape, number and arrangement of the X-ray markers.

It will also be appreciated that the marker elements according to the invention may not only be introduced into openings provided specifically for same in the wall of the stent. Equally they can advantageously be introduced into openings predetermined by the mesh structure of the wall of the stent. In that case they can be distributed as desired over the stent.

What is claimed is:

1. A method of applying a marker element to an implant intended for implantation in a human or an animal body, said implant comprising a main body and an opening provided in said main body for receiving the marker element, comprising the steps of:

introducing a hardenable material or material mix into the opening; and hardening the hardenable material or material mix therein to form at least a part of the marker element;

wherein both the introducing step and the hardening step are effected by galvanic deposit.

2. A method of applying a marker element to an implant intended for implantation in a human or an animal body, said implant comprising a main body and an opening provided in said main body for receiving the marker element, comprising the steps of:

introducing a granular solid material or material mix into the opening, and sintering the granular solid material or material mix therein to form at least a part of the marker element.

3. The method according to claim 2, wherein the step of sintering the solid granular material or material mix includes applying process energy locally in the region of the opening.

4. The method according to claim 3, wherein at least a part of the process energy is introduced by targeted irradiation in the region of the opening.

5. The method according to claim 4, wherein the targeted irradiation is laser radiation.

6. The method according to claim 3, wherein at least a part of the energy is introduced by ultrasound.

7. The method according to claim 2, wherein the step of sintering the solid granular material or material mix includes applying process energy electrically by producing a flow of current through the material or material mix arranged in the region of the opening.

* * * * *